(12) United States Patent
Kwik et al.

(10) Patent No.: US 12,727,932 B2
(45) Date of Patent: Sep. 8, 2026

(54) METHOD FOR OPERATING AN ELECTROSURGICAL GENERATOR AND ELECTROSURGICAL GENERATOR

(71) Applicant: OLYMPUS WINTER & IBE GMBH, Hamburg (DE)

(72) Inventors: Anne Kwik, Berlin (DE); Fabian Stopp, Berlin (DE); Jens Krüger, Zeuthen (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 460 days.

(21) Appl. No.: 18/392,047

(22) Filed: Dec. 21, 2023

(65) Prior Publication Data

US 2024/0206949 A1 Jun. 27, 2024

Related U.S. Application Data

(60) Provisional application No. 63/434,997, filed on Dec. 23, 2022.

(51) Int. Cl.
*A61B 18/12* (2006.01)
*A61B 18/00* (2006.01)
(Continued)

(52) U.S. Cl.
CPC .......... *A61B 18/1206* (2013.01); *A61B 34/25* (2016.02); *G06F 21/1077* (2023.08);
(Continued)

(58) Field of Classification Search
CPC ........ A61B 18/1206; A61B 2018/1823; A61B 2018/00589; A61B 2018/00601;
(Continued)

(56) References Cited

U.S. PATENT DOCUMENTS 7,730,529 B2 6/2010 Zunke
2020/0008859 A1 1/2020 Cadouri et al.
(Continued)

FOREIGN PATENT DOCUMENTS

DE 10 2019 103 445 A1 8/2020
EP 2 068 740 B1 4/2019

OTHER PUBLICATIONS

May 1, 15, 2024 Search Report issued in European Patent Application No. 23216802.1.

*Primary Examiner* — Ronald Hupczey, Jr.
(74) *Attorney, Agent, or Firm* — Oliff PLC

(57) ABSTRACT

A method for operating an electrosurgical generator and an according electrosurgical generator. Electrosurgical generator is configured to supply power to electrosurgical instrument. Electrosurgical generator is identifiable by serial number and includes at least two modules. Modules are embodied as hardware and or software modules. Each module functions according to operation mode wherein at least partially specified by license key. In initializing process of electrosurgical generator, identification information being indicative of serial number is available or made available at at least one module and license information being indicative of license key is available or made available at at least one module. Each module provides any identification and license information being available or being made available to it to at least one other module. At least one module generates a link of identification and license information and provides generated link to each of the other modules. Each module stores generated link.

17 Claims, 6 Drawing Sheets

Figure 1:
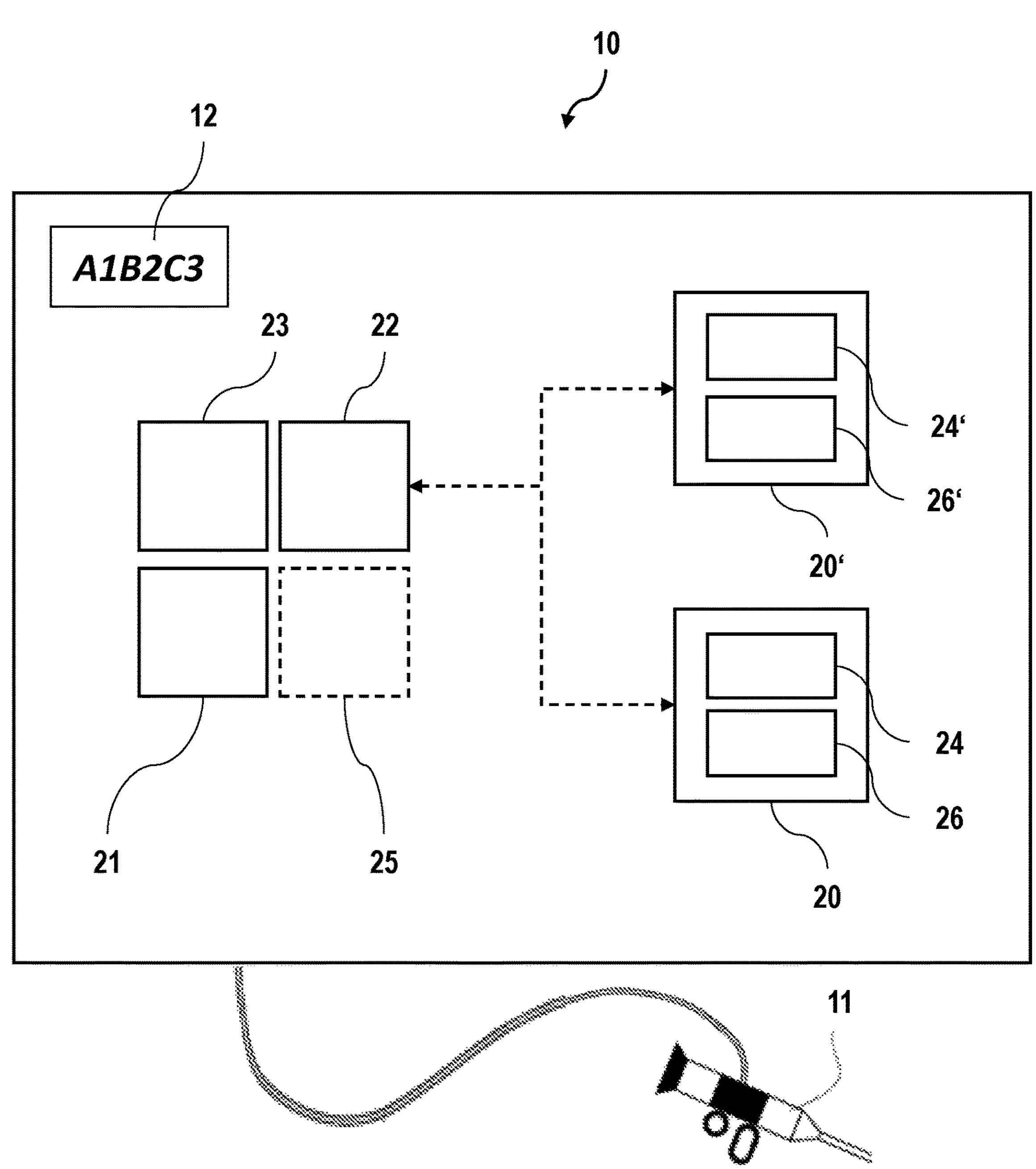

(51) Int. Cl.
*A61B 34/00* (2016.01)
*G06F 21/10* (2013.01)

(52) U.S. Cl.
CPC ............... *A61B 2018/00589* (2013.01); *A61B 2018/00601* (2013.01); *A61B 2018/00607* (2013.01); *A61B 2018/00702* (2013.01); *A61B 2018/00767* (2013.01)

(58) Field of Classification Search
CPC ............ A61B 2560/0266; A61B 90/98; G06F 21/1077; G06F 20/40; G06F 40/63
See application file for complete search history.

(56) References Cited

U.S. PATENT DOCUMENTS

2020/0046416 A1 2/2020 Ellman et al.
2021/0374215 A1 12/2021 Nissen et al.
2022/0104843 A1 * 4/2022 Shelton, IV ........... A61B 17/32

* cited by examiner

METHOD FOR OPERATING AN ELECTROSURGICAL GENERATOR AND ELECTROSURGICAL GENERATOR

The invention relates to a method for operating an electrosurgical generator and an electrosurgical generator.

In electrosurgery or high-frequency surgery, an electrosurgical instrument such as an electroscalpel is used to apply high-frequency alternating current to tissue in the human body, in particular to cut or sever the tissue by heating it and to remove tissue by thermal resection. One advantage of this is that bleeding can be stopped at the same time as the cut by closing the affected vessels, and electrosurgical instruments can be used for other applications, such as coagulation. Electrosurgical generators are used to supply power to electrosurgical instruments and are designed to deliver a high-frequency alternating voltage to an electrosurgical instrument, so they are medical devices. Such generators can be of modular design with individual modules which provide functionality independent from each other, e.g., modules contributing in supplying power to the electrosurgical instrument, socket modules for connection of the electrosurgical instrument and a gas supply module, in particular supplying Argon.

The modules of an electrosurgical generator can be exchanged and replaced independently as required. However, if the electrosurgical generator is provided with a customized functionality scope requiring each of its modules to operate only within specific parameters, and a module of said generator is to be exchanged, a newly installed module does not have the necessary information about the specific parameters for it to operate within according to the customized functionality scope of the generator.

It is therefore a task of the present invention, against the background of the above-mentioned problems, to provide an improved method for operating an electrosurgical generator, which in particular enables improved control of a newly installed module of a plurality of modules of the electrosurgical generator.

The solution according to the invention is within the features of the independent claims. Advantageous embodiments are subject of the dependent claims.

According to the invention a method for operating an electrosurgical generator configured to supply power to an electrosurgical instrument is disclosed, the electrosurgical generator being identifiable by a serial number and comprising at least two modules, wherein the modules are embodied as hardware modules and/or as software modules, wherein each of the modules has a functionality according to an operation mode which is at least partially specified by a license key, wherein in an initializing process of the electrosurgical generator, identification information being indicative of a serial number is available or is made available at at least one of the modules and license information being indicative of a license key is available or is made available at at least one of the modules, each of the modules provides any of the identification information and the license information being available or being made available to it to at least one other of the modules, at least one of the modules generates a link of the identification information and the license information and provides the generated link to each of the other modules, and each of the modules stores the generated link.

The invention is likewise directed to an electrosurgical generator, configured to supply power to an electrosurgical instrument and being identifiable by a serial number, comprising a processor, a communication interface, and at least two modules, wherein each of the modules has a functionality according to an operation mode which is at least partially specified by a license key and comprises a data storage for storing at least a link of a license information indicative of the license key and an identification information indicative of the serial number and a communication interface, the electrosurgical generator further comprising a computer-readable medium, the medium having stored therein instructions which, when executed by the processor, cause the method according to the invention to be performed.

The electrosurgical generator is provided with a plurality of at least two modules, for example dependent on a specific use scenario or on a user-specific functionality. The modules are embodied as hardware modules and/or as software modules. The electrosurgical generator may include, for example, a power supply module that, in operation, feeds a DC circuit, and an inverter module that is fed by the DC circuit and generates a high-frequency AC voltage that is applied to output modules for connection to an electrosurgical instrument. Typical electrosurgical instruments include electric knives and electric scalpels.

The invention provides a beneficial method for operating an electrosurgical generator, which makes use of an existing modular design of the generator to provide the modules of the electrosurgical generator with information about a customized scope of functionality for them to provide. The method may be performed during or as part of a boot process of an electrosurgical generator, for instance the first boot process after replacement of a module of the generator. The method takes advantage of the fact that typically several modules of a generator have information available, which indicates an identity of the generator in which the modules are installed, or which information indicates a customized scope of functionality intended for the modules of the respective generator. The customized scope of functionality for a module of a generator, preferably for each of the modules of a generator, may be characterized by an operation mode that is defined by a license key, which is exemplarily linked to the identity of the generator. The method makes it possible for a newly installed module to participate in information that is already available at other modules of the generator and that can be used to define the scope of functionality also of the newly installed module. If no such information is available at the modules, the according information may be made available, for example under consideration of according user input.

In this way, a module newly installed in the generator can be provided with a functionality according to an operation mode that allows it to be operated according to a specified functionality scope. This can be achieved reducing time-consuming individual or even manual adjustment of the permissible operating parameters, and the effort required to operate the generator comprising the module can be substantially reduced.

In the following, some expressions that are used within the context of the invention are explained first:

Each of the at least two modules is configured to operate with a functionality according to an operation mode, for example an operation mode of a plurality of predetermined operation modes of the respective module of the electrosurgical generator. The operation mode defines the scope of functionality for each of the modules installed in the electrosurgical generator. The operation mode is at least partially specified by a license key, which can thus be associated with a specific functionality of a particular module. For example, for each of the plurality of operating modes, e.g., the operating modes specifiable by a license key, a representation of the respective operating mode may be stored in a data storage of the module. The operation mode may specify the functionality of a module according to operating parameters, for example an operating parameter range, according to which the module can be operated. Exemplary operating parameters include powers, voltages, currents or frequencies to be provided by a module, for instance dependent on an individual capability of the module. An operating parameter may be characterized by a measured variable.

The modules are configured to provide or to be provided with identification information, license information and a link of an identification information and a license information, which may thus be sent or received by a module. For this purpose, a module comprises at least one wireless and/or wired communication interface. Also, the electrosurgical generator includes at least one wireless and/or wired communication interface, which may be configured, for example, as an individual module or as part of a module. By means of the communication interface, for example, transmission and/or reception can take place via a wireless and/or wired communication link. A communication link is to be understood as a channel according to a communication technique, via which data can be sent and received, comprising a representation of an identification information, a license information or a link of an identification information and a license information. The communication link may be an at least partially secured communication link. Exemplary communication links are radio channels (known to the skilled person e.g., under the acronyms RFID, NFC, Bluetooth or WLAN), mobile data links (known to the skilled person e.g., under the acronyms GSM, UMTS or LTE) or wired communication links known to the skilled person e.g., as a local area network or as a bus system (e.g., CAN bus or USB). The communication link may comprise one or more nodes, for example routers, along which it runs at least in part.

The modules, and optionally also the electrosurgical generator, comprise a data storage for storing at least the link of an identification information and a license information. The identification information and/or the license information may be stored on a data storage of the module, as well. The data storage of a module can be portable or integrated in the module.

The identification information is indicative of a serial number, by which an electrosurgical generator can be identified. The serial number is representative of a specific, preferably unique, identity of an electrosurgical generator. It is also conceivable that the serial number is representative of an electrosurgical generator of a specific type. The serial number may also be, for example additionally, representative of a designated location of use of the electrosurgical generator. Exemplarily, the serial number may be indicated by a unique identifier of a generator.

The license key may be linked to a serial number, in particular the serial number, of which the identification information is indicative. For example, two different license keys may specify different operation modes or may specify corresponding, e.g., matching, operation modes but be linked to different serial numbers. The license information may indicate a customized scope of functionality intended for a module, which may be characterized by an operation mode that is specified by a license key. The license key is linked to a serial number indicating the identity of a generator.

Accordingly, the identification information, indicative of the respective serial number, and the license information, indicative of the respective license key, can be combined in a link. To generate such a link identification information and license information may for example be combined in a linked information. In particular, the identification information and the license information may be combined in the linked information such that the respective identification information and license information can be determined from the linked information. For this purpose, the modules may have a suitable processor. For example, the link is generated by at least one of the modules, to which the identification information and the license information has been provided.

Under the availability of information, such as identification information, license information or a link of an identification information and a license information, is to be understood for example the retrievability of the respective information from the data storage of the module or from a cloud data storage, which may for example be located separately from the electrosurgical generator.

An initialization process is to be understood for example as a process within the scope of the initial start-up after installation of the electrosurgical generator.

Making available the identification information or the license information at a module of the electrosurgical generator may comprise obtaining the respective information via a user interface of the electrosurgical generator. The obtaining may be achieved for example by capturing a user input at the user interface. The user interface may be integrated in or external to the electrosurgical generator. Examples of a user interface include a button, keypad, keyboard, mouse, display unit (e.g., display, microphone, touch-sensitive display unit (e.g., touchscreen and/or touch display), speaker, camera, and/or touch-sensitive surface (e.g., touchpad). The user interface may be configured, for example, as a module or as part of a module.

For example, the electrosurgical generator provides, e.g., presents to a user, by means of the user interface a prompt for user input, for example as part of a user dialog. In the exemplary case of making available the identification information, a prompt is provided for indicating a serial number. In another exemplary case of making available the license information, a prompt is provided for indicating a license key. In reaction of the prompt, the electrosurgical generator may then capture the user input, which may include an indication of a value and/or a selection from one or more choices (e.g., a multiple-choice prompt). The respective information may then be obtained by determining the identification information and/or the license information dependent on the captured user input.

Also, making available an information at a module can be done, for example, by means of the communication interface of the module, optionally using the communication interface of the electrosurgical generator as well. It is for example conceivable that an information is made available to a module by receiving an according information that has been captured at a user interface separate from the electrosurgical generator by means of the communication interface of the generator and providing the respective information to the module via the communication interface of the module.

According to an embodiment the method further comprises: determining a checking identification information from the identification information available at at least one of the modules, determining a checking license information from the license information available at at least one of the modules, and determining a checking link of an identification information and a license information from the links stored at at least one of the modules; checking, dependent on the checking identification information and the checking license information, whether the checking link is valid; and if the result of the checking is positive, providing the checking link to each of the modules as a valid link; and storing the valid link at each of the modules.

In this way it can be achieved that if a link stored at one of the modules of the electrosurgical generator is checked as valid, it is made available at all modules of the generator.

The determining of the checking identification information, the checking license information and the checking link may for example be done on the basis of an arbitrary selection from the identification information, the license information and the stored links from available at the modules or on the basis of predefined selection criteria. For example, it is conceivable that the checking identification information, the checking license information and the checking link are determined from identification information, license information, and stored links originating from different modules, if possible, or it is preferred to consider information and link from one single module of the electrosurgical generator, e.g., from a master module, if possible.

Checking whether a checking link of an identification information and a license information is valid is to be done dependent on a checking identification information and a checking license information. For checking the validity of the checking link it is checked whether checking license information and the checking identification information match with the identification information and the license information of the checking link. That is, it is checked whether the license key indicated by the checking license information and the serial number indicated by the checking identification information correspond to the ones that are indicated by the identification information and the license information, which are linked in the checking link. If this is the case, the checking link is considered valid, and the result of the checking is positive. If the checking link is considered not valid, the result of the checking is negative. By matching it is to be understood that the information checked for matching correspond to each other according to predetermined rules, and are preferably the same, in particular identical.

It is also conceivable that for the checking of the validity of a checking link the respective checking information are transmitted from one or more modules, for example, using the communication interface of the modules, and optionally also the communication interface of the generator, to a separate entity, such as a server or a smartphone. The modules can then receive, in reaction of the transmission, in particular from the separate entity, to which the checking identification information and checking operation information have been transmitted, a resulting information with which the result of the checking can be determined.

For providing according checking and determining functionality, determination and/or selection rules may be specified that predetermine if a license key is valid for a specific serial number. The predetermined determination and/or selection rules are, exemplary, in the form of one or more tables that assign license information to, for example, identification information and/or a combination of identification information. For example, one or more representations of such tables are stored in one or more of the modules. It is also conceivable that a module can get access to determination and/or selection rules available, e.g., stored, in a separate entity or in another module of the electrosurgical generator, for example using the communication interface of the module and optionally also the communication interface of the generator, by means of appropriate program instructions.

If the result of the checking whether the checking link is valid is negative, the step of checking, dependent on the checking identification information and the checking license information, whether the checking link is valid, may be repeated, wherein another checking link, for example a checking link available at another module, is determined. The repeating may be performed until the checking links available at all modules of the generator have been checked.

This allows to ensure that, if available, further, e.g., all, links present in the modules of the generator are checked for validity.

Additionally, determining a checking link of an identification information and a license information from the links stored at at least one of the modules may comprise: checking, whether a link is stored at more than one of the modules; if the result of the checking is positive, determining, from the stored links, the checking link based on a majority decision, and if the result of the checking is negative, determining the stored link as the checking link.

This allows to add an additional verification step for the link that is to be considered as the checking link. If the links stored on different modules should be dissimilar, it can be ensured that such stored link is taken into account as checking link, which is present on the largest part of modules. This situation can occur, for example, if a newly installed module is taken over from another electrosurgical generator and therefore may have a link stored thereon, which is based on identification information that does not indicate the serial number of the electrosurgical generator, into which the module is installed. In this case, only such link will be determined as checking link, that is present on a majority of modules, i.e. of the modules, which have remained unchanged in the electrosurgical generator. If no majority can be reached for a majority decision, one of the stored links may be randomly determined as the checking link. If a link is stored on only one module of the electrosurgical generator, which may be the case for a new generator coming out of the factory, e.g., comprising a master module as the only module having an identification information available, this single link will be considered for the validity check.

Optionally, if the result of the checking whether the checking link is valid is negative, the method may further comprise: checking, whether matching identification information and matching license information are available at more than one, preferably at a majority, of the modules; and if the result of the checking is positive, then generating a link of the matching identification information and the matching license information and providing the generated link to each of the modules as a valid link.

In a case where the checking link has been checked as invalid, but matching identification information and license information, on which the checking has been based, are available on a plurality of modules, this multiple availability of matching respective information can be used to conclude with sufficient probability that the identification information and license information are valid, so that a link that is also valid with sufficient probability is generated.

Exemplarily, if the result of the checking whether the checking link is valid is negative, the method further comprises: determining, if the checking identification information matches with the identification information, based on which the checking link is generated and if the checking license information matches with the license information, based on which the checking link is generated; if the checking identification information is determined to not match with the identification information, based on which the checking link is generated, and the checking license information is determined to match with the license information, based on which the checking link is generated, checking, whether an affirmed identification information can be determined based on identification information and/or a link of an identification information and a license information available to or stored at the modules, if the result of the checking is positive, determining the affirmed identification information as a second checking identification information, and if the result of the checking is negative, obtaining a second checking identification information via a user interface of the electrosurgical generator; generating a checking link of the second checking identification information and the checking license information, providing the checking link to each of the modules as a valid link; and storing the valid link at each of the modules. Exemplarily, these steps are only performed in case no valid link can be determined at, for example each of, the modules of the generator.

An information shall be considered as affirmed, if the respective information available at more than one, preferably at a majority, of the modules of the electrosurgical generator are indicative of matching serial numbers or license keys.

Additionally or alternatively, if the result of the checking whether the checking link is valid is negative, the method may comprise: determining, if the checking identification information matches with the identification information, based on which the checking link is generated and if the checking license information matches with the license information, based on which the checking link is generated; if the checking license information is determined to not match with the license information, based on which the checking link is generated, and the checking identification information is determined to match with the identification information, based on which the checking link is generated, checking, whether an affirmed license information can be obtained based on license information and/or a link of an identification information and a license information available to or stored at the modules, if the result of the checking is positive, determining the affirmed license information as a second checking license information, and if the result of the checking is negative, obtaining a second checking license information via a user interface of the electrosurgical generator; generating a checking link of the second checking license information and the checking identification information, providing the checking link to each of the modules as a valid link; and storing the valid link at each of the modules. Exemplarily, these steps are only performed in case no valid link can be determined at, for example each of, the modules of the generator.

Further additionally or alternatively, if the result of the checking whether the checking link is valid is negative, the method may comprise: determining, if the checking identification information matches with the identification information, based on which the checking link is generated and if the checking license information matches with the license information, based on which the checking link is generated; if the result of both steps of determining is negative, checking, whether an affirmed identification information and an affirmed license information can be obtained based on identification information, license information and/or a link of an identification information and a license information available to or stored at the modules, if the result of the checking is positive, determining the affirmed identification information as a second checking identification information and the affirmed license information as a second checking license information, and if the result of the checking is negative, obtaining the second checking identification information and the second checking license information via a user interface of the electrosurgical generator; generating a checking link of the second checking identification information and the second checking license information, providing the checking link to each of the modules as a valid link; and storing the valid link at each of the modules. Exemplarily, these steps are only performed in case no valid link can be determined at, for example each of, the modules of the generator.

In case that the validity checking of the checking link is negative due to a non-matching serial number and/or a non-matching license key, a second checking identification information and/or a second checking license information may be obtainable from affirmed identification information and/or license information available at other modules than the ones, from which the respective checking information have been determined. Alternatively, a second checking identification information and/or a second checking license information may be obtained via according input into a user interface of the generator. These scenarios may occur for example when the identification information and/or the license information of a module newly installed into the electrosurgical generator is determined as checking information, wherein the identification information available at the module does not indicate the serial number that identifies the electrosurgical generator, into which it is installed, but e.g., a different electrosurgical generator and/or wherein the license information available at the module does indicates a license key that is not linked to the identity of the generator according to its serial number.

Accordingly, even in the case of a negative validity check, it is possible to fall back on correct information that may nevertheless be available for modules of the generator, on the basis of which a valid link can be generated and made available to all modules.

According to an embodiment, one of the modules of the electrosurgical generator is designed as a master module, which is configured to have the identification information available by having stored the identification information or by obtaining the identification information via the user interface of the electrosurgical generator, and wherein the identification information available at the master module is provided to each of the other modules and/or wherein the checking identification information is determined from the identification information available at the master module.

Optionally, the master module is configured to have at least the identification information available for providing it to at least one of the other modules of the generator. Such providing may be done as part of the initialization process. Additionally or alternatively, the identification information available at the master module is determined to be the checking identification information in a validity check of the checking link of identification information and license information.

A configuration of the electrosurgical generator comprising a module designed as such a master module allows the identification information to be provided, and e.g., managed, centrally, so that generally no identification information is required to be individually and separately available, for example stored, at the other modules. The other modules, in turn, may have a less elaborate structure, for example their data storage can be designed less complex, because the identification information does not have to be stored.

Additionally, the license information is available at the master module, preferably as a stored information, or the license information is made available at the master module by obtaining the license information from at least one of the other modules or by obtaining the license information via the user interface of the electrosurgical generator, wherein the identification information available at the master module is determined as a checking identification, wherein the license information available or made available at the master module is determined as a checking license information, and wherein the checking link of an identification information and a license information from the links stored at at least one of the modules is determined by generating, at the master module, a master link of the identification information available at the master module and the license information available at the master module and determining the master link as the checking link.

In this embodiment, the license information may also be available at the master module so that a master link of identification information and license information can be generated directly based on the information available at the master module. As the master link is accordingly generated based on the checking identification information and the checking license information, it will be checked as valid and provided to the other modules and stored there.

Optionally, the method may further comprise: checking, whether at any of the modules an identification information or a link of an identification information and a license information is available; providing the identification information available at the master module to each of the modules, at which an identification information is not available, and providing the checking link generated at the master module to each of the modules, at which a link of an identification information and a license information is not available; and, preferably, if an identification information is not available at the master module, obtaining the identification information via the user interface of the electrosurgical generator.

This allows for a distribution of the identification information available at the master module to modules, at which no identification information is available, so that e.g., the identification information of the master module may be used or stored there, for example to be used there for generating a link. This scenario may occur when a new module is installed into the electrosurgical generator, which may for example be out of the factory and thus may not have any identification information available. In case the master module itself is such a newly installed module without available identification information, the identification information can be obtained by user input.

In addition, the method may further comprise: receiving, at the master module, any of the links of an identification information and a license information stored at the other modules; checking, dependent on the identification information and the license information available at the master module, whether the received links are valid; and if the result of any of the checking is negative, making available a license information at the master module by obtaining the license information via the user interface of the electrosurgical generator.

This scenario considers in particular a new installation of a master module into a generator in that the master module may receive the correct license information from the other modules and check their validity based upon the information available at the master module. If the result of a check is negative, the correct license information can be obtained via user input. In this embodiment, the other modules do not have to be configured for generating a link of identification information and license information, which allows a less complex design of those modules.

In an embodiment, each of the modules is configured to have the identification information and the license information available, further comprising: obtaining identification and/or license information via the user interface of the electrosurgical generator or obtaining identification and/or license information from at least one of the modules and providing the obtained identification and/or license information to any of the modules, at which the respective information is not available; generating, at each of the modules, a link of the identification information and the license information available at the respective module and storing the generated link.

In this way, it can be ensured that, with a corresponding configuration of the modules, each module is provided with the identification information and license information and is thus able to generate a link of an identification information and a license information. This allows for implementing a modular electrosurgical generator with a decentralized information availability.

Additionally, the obtaining identification information may comprise providing, to each of the modules, the identification information available at the master module; and the method may further comprises: determining, at each of the modules, dependent on the provided identification information and the license information available at the respective module, if the stored link of an identification information and a license information at the respective module is valid.

By implementing such method steps, it is possible to verify the stored link at each of the modules based on the identification information available at the master module. In other words, the license information available at each of the modules is checked for validity. If the result of the checking is negative for a specific module, an affirmed license information may be obtained via a user interface of the electrosurgical generator or from at least one of the other modules, and the checking may be repeated. If the result of the checking is positive for a specific module, the stored link may be considered as a valid link.

Exemplarily, an identification information may be available at each of the modules, and the method may further comprise: checking, whether the identification information available at each of the modules are matching, and, if the result of the checking is negative, obtaining an identification information via a user interface of the electrosurgical generator; and checking whether a license information is available at at least one of the modules, and if the result of the checking is positive, generating a link of the identification information and the license information, providing the generated link to each of the modules and storing the generated link at each of the modules.

With such an embodiment, a decentralized structure can be implemented, in which the identification information is available at each module, e.g., stored, together with the link of this identification information and a license information, wherein the license information may be provided by any of the modules of the generator, for example by a module that is particularly configured to provide the license information, such as a replaceable license key storage module that might for example be installed only temporarily, e.g., specifically during a validity check.

According to an embodiment, the method further comprises: providing, at each of the modules, a functionality according to an operation mode which is at least partially specified by the license key of which the license information of the valid link is indicative.

In this way, it can be ensured that the module can be operated properly if a link has been checked as valid.

Alternatively or additionally, if the result of the validity checking is negative, the module may effect an output of an according signal, for example by means of a suitable user interface of the module or of the electrosurgical generator. It is also conceivable that the signal is sent by means of the communication interfaces of the electrosurgical generator and/or of the module. By such a signal, the user may be notified that no valid link is available at a module, for example via the user interface or via a device configured to receive the sent signal.

The invention also includes a computer program comprising program instructions to cause a processor to execute and/or control the method according to the invention when the computer program is executed on the processor.

The computer program according to the invention is stored, for example, on a computer-readable data carrier.

It is to be understood that the presentation of the invention in this section is merely by way of examples and non-limiting.

The invention is explained in more detail below by way of examples in conjunction with the accompanying drawings, showing advantageous embodiments.

Figure 2:
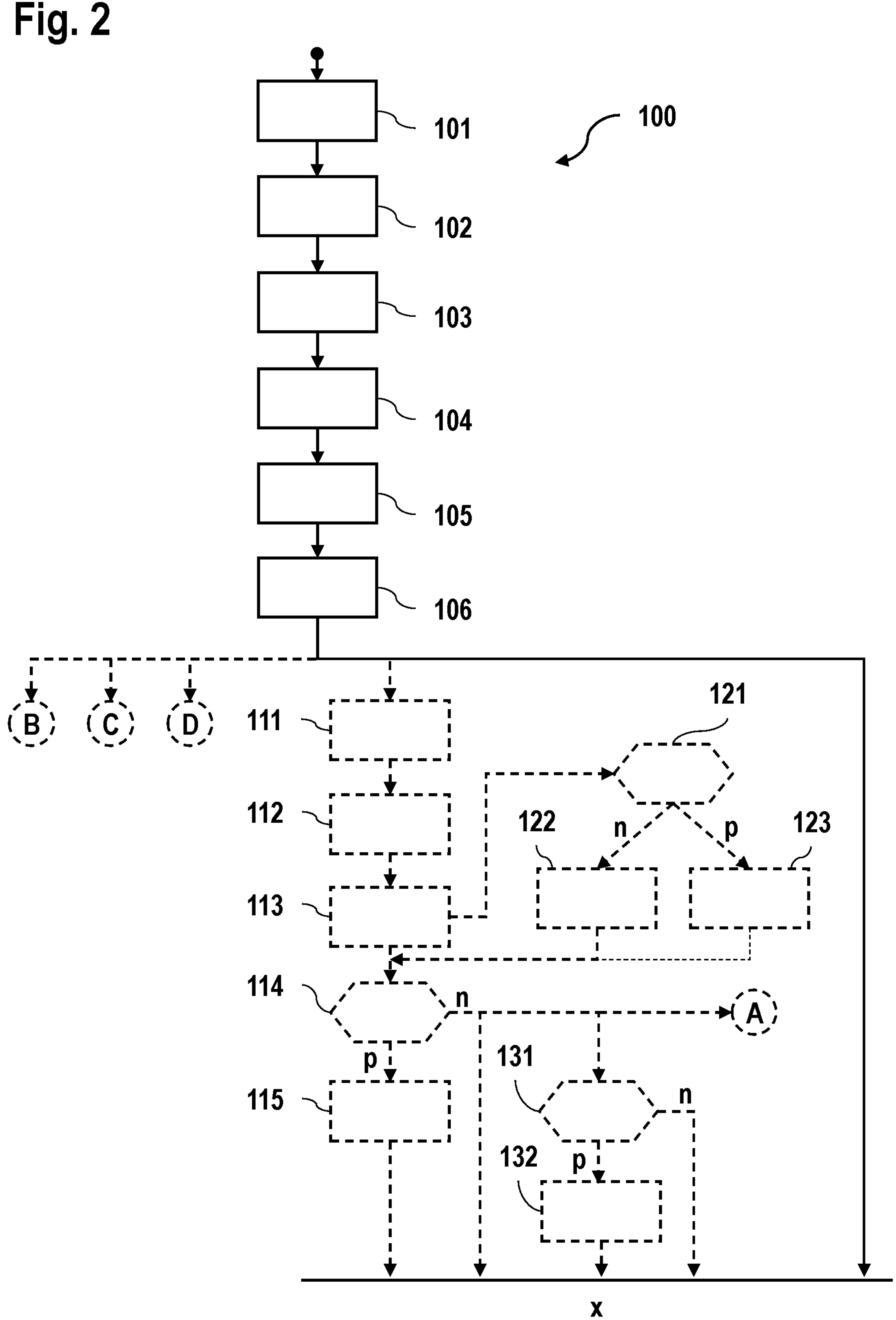

In the figures show:

FIG. 1 a schematic representation of an electrosurgical generator according to an embodiment;

FIG. 2 a schematic flow diagram of a method according to an embodiment; and

FIGS. 3-6 schematic flow diagrams of sections of methods according to embodiments.

FIG. 1 shows a schematic representation of an electrosurgical generator 10 for supplying power to an electrosurgical instrument 11. The instrument 11 is, by way of example, an electroscalpel. The generator 10 comprises two modules 20, 20', which may be embodied as hardware modules and/or as software modules, and which are configured to operate with a functionality according to an operation mode that is defined by a license key. The electrosurgical generator 10 comprises a unique serial number 12 that represents the identity of the generator 10. The generator is thus identifiable by the serial number 12. The serial number 12 is provided in the form of a tag on the case of the generator 10.

The electrosurgical includes a processor 21, a communication interface 22, a data carrier 23 and a user interface 25. Each of the modules 20, 20' comprises a data storage 24, 24' and is designed to communicate via a communication link by means of a communication interface 26, 26' e.g., with other modules 20, 20' and also with communication interface 22 of the electrosurgical generator 10. The electrosurgical generator 10 may comprise further modules that may also be configured to communicate with the modules 20, 20' and with the generator 10. On the data storage 24, 24', a link is stored of a license information indicative of the license key and an identification information indicative of a serial number 12. The designs of the functional units (processor, communication interface, data storage, data carriers) of the generator 10 and of the modules 20, 20' are not described in more detail below since they are within the scope of the knowledge of the skilled person. For example, it is readily familiar to the skilled person to resort to commonly used memory types (RAM, ROM, EEPROM) in the design of the data storage 24, 24 and the data carrier 23.

FIG. 2 illustrates a schematic flow diagram of a method 100 according to an embodiment for operating an electrosurgical generator 10 as described above. The electrosurgical generator 10 is identifiable by a serial number 12 and comprises at least two modules 20, 20', wherein each of the modules 20, 20' has a functionality according to an operation mode which is at least partially specified by a license key. The method 100 is executed in an initialization process within the initial start-up after installation of the electrosurgical generator 10.

In a step 101, identification information being indicative of a serial number 12, by which an electrosurgical generator such as the generator 10 can be identified, is available or is made available at at least one of the modules 20, 20'. In a step 102, license information being indicative of a license key is available or is made available at at least one of the modules 20, 20'. The license information indicates a customized scope of functionality intended for each of the modules 20, 20' of the electrosurgical generator 10, which functionality is characterized by an operation mode that is specified by a license key, such as the license key specifying the operation mode, according to which the functionality of the modules 20, 20' of the generator 10 is provided.

The identification information and/or the license information may stored at the data storage of a module or be made available at a module by obtaining the respective information via the user interface 25 of the electrosurgical generator 10. For obtaining an identification information, the user interface 25, being configured as a touch-sensitive display, prompts the user for user input indicating a serial number. The user interface 25 captures the user input that is made in reaction of the prompt, so the identification information that is determined dependent on the captured user input will be indicative of the serial number. Correspondingly, for obtaining a license information, the user interface 25 prompts the user for user input indicating a license key. The user interface 25 captures the user input that is made in reaction of the prompt, so the license information that is determined dependent on the captured user input will be indicative of a license key specifying an operation mode according to which the functionality of the modules 20, 20' of the generator 10 is provided.

Each of the modules 20, 20' provides, in step 103, any of the identification information and the license information being available or being made available to it in steps 101 and 102 to at least one other of the modules 20, 20'. Accordingly, the modules 20, 20' are configured to send and to receive an identification information and a license information, for which purpose, the modules 20, 20' module comprise at least one wireless and/or wired communication interface 26, 26'.

In step 104, at least one of the modules 20, 20', to which the identification information and the license information has been provided, generates a link of the identification information and the license information.

The generated link is then provided to each of the other modules 20, 20' in a step 105 by using the communication interfaces 26, 26' of the modules for sending and receiving, respectively, the generated link. The generated link provided to each of the modules 20, 20' in step 105 is then stored in step 106 at each of the modules 20, 20' at their respective data storage 24, 24'.

Additionally, in the presented embodiment, a validity check of the stored links is provided. Such a validity check is particularly advantageous if an exchange of modules 20, 20' has taken place after the initialization process according to the steps 101-106, and the stored links at the modules 20, 20' of the generator 10 may not match, or not be present at all.

For this purpose, a checking identification information is determined in a step 111 from the identification information available at at least one of the modules 20, 20', a checking license information is determined in a step 112 from the license information available at at least one of the modules 20, 20' and a checking link of an identification information and a license information is determined in a step 113 from the links stored at at least one of the modules 20, 20'.

The checking link is determined in step 113 by checking, in a step 121, whether a link is stored at more than one of the modules 20, 20'. If this is not the case, this one stored link is determined as the checking link in a step 122. If this is the case, and a link is stored at at least two modules, the checking link is determined based on a majority decision in a step 123. If no majority can be reached for a majority decision, one of the stored links will be randomly determined as the checking link.

In a step 114, dependent on the checking identification information determined in step 111 and the checking license information determined in step 112, checking is performed whether the checking link determined in step 113 is valid. If the result of the checking 114 is positive, the checking link is provided in a step 115 to each of the modules 20, 20' as a valid link, which is then stored at each of the modules 20, 20'.

If the result of the checking 114 whether the checking link is valid is negative, it is additionally checked in a step 131, whether matching identification information indicating matching serial numbers and matching license information indicating matching license keys are available at a majority of the modules 20, 20'.

If this is the case, i.e., if the result of the checking 131 is positive, a link of the corresponding identification information, and the corresponding license information is generated and provided to each of the modules 20, 20' as a valid link in a step 132.

Figure 3:
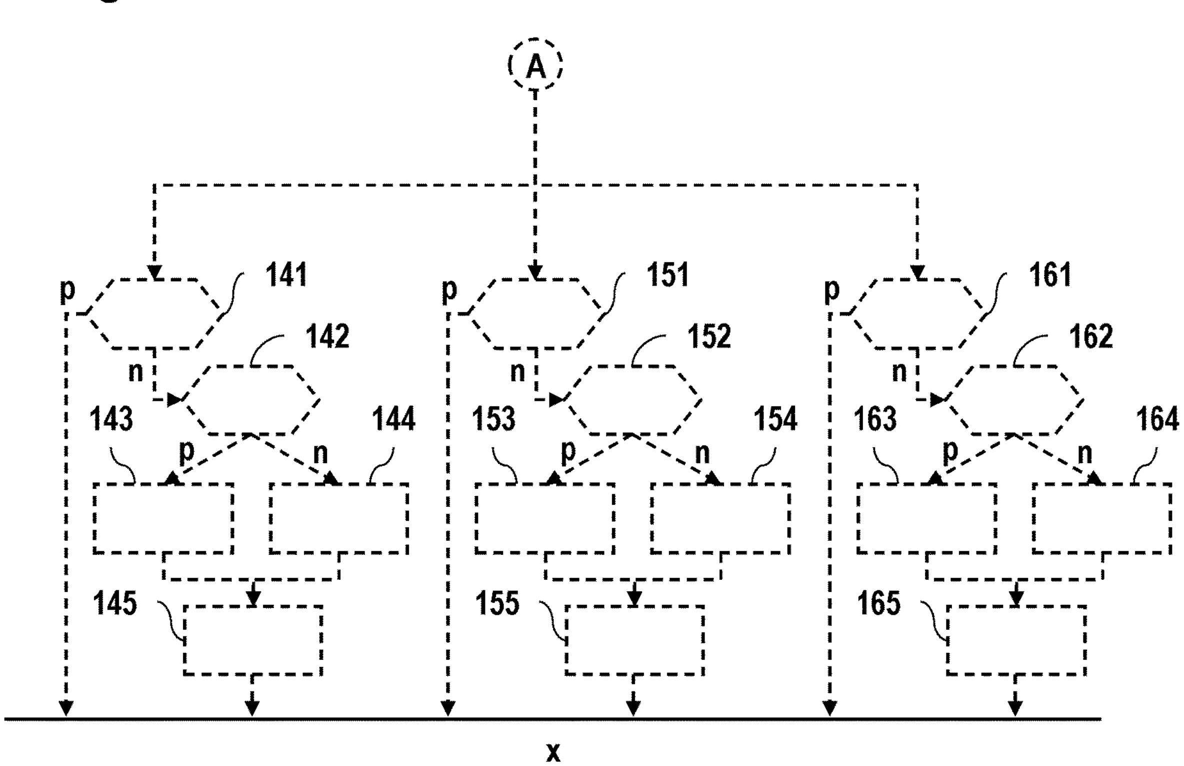

If the result of the checking 114 whether the checking link is valid is negative, the method 100 may also comprise a method part A, as illustrated by way of the exemplary schematic flow diagram of a section of the method 100 in FIG. 3. The method part A describes additional or alternative method steps in order to achieve a valid link of identification information and license information under consideration of different scenarios for the link to be checked as invalid in step 114. The exemplarily scenarios considered in method part A take into account a missing match of the serial numbers indicated by the checking identification information and by the identification information that is linked to the license information in the checking link, a missing match of the license keys indicated by the checking license information and by the license information that is linked to the identification information in the checking link and both missing matches of serial numbers and license keys.

Accordingly, in a step 141 it is determined, if the checking identification information, as determined in step 111, matches with the identification information, based on which the checking link, as determined in step 113, has been generated. It is also determined in step 141, if the checking license information, as determined in step 112, matches with the license information, based on which the checking link, as determined in step 113, is generated.

If only the indicated serial numbers are non-matching but the indicated license keys do match, it is checked in a step 142, whether an affirmed identification information can be obtained based on identification information and/or a link of an identification information and a license information available to or stored at the modules 20, 20'. An information is considered as affirmed, if the respective information available at a majority of the modules 20, 20' of the electrosurgical generator 10 are indicative of matching serial numbers and license keys, respectively.

If the result of the checking 142 is positive, the affirmed identification information is determined as a second checking identification information in a step 143. In case of a negative result of the checking 142, a second checking identification information is obtained via the user interface 25 of the electrosurgical generator 10 in a step 144.

In a step 145, a checking link of the determined or obtained second checking identification information and the checking license information is generated and provided to each of the modules 20, 20' as a valid link and stored at each of the modules 20, 20'.

In an analogous way to the verification of the checking link with respect to the identification information in steps 141-145, a verification of the checking link with respect to the license information, as it is the subject-matter of steps 151-155, may be performed alternatively or additionally.

Analogously to step 141, it is determined in step 151, if the checking identification information matches with the identification information, based on which the checking link is generated and if the checking license information matches with the license information, based on which the checking link is generated. Vice versa to step 142, it is checked in step 152, whether an affirmed license information can be obtained based on license information and/or a link of an identification information and a license information available to or stored at the modules 20, 20' if the checking license information is determined 151 to not match with the license information, based on which the checking link is generated, and the checking identification information is determined 151 to match with the identification information, based on which the checking link is generated. If the result of the checking 152 is positive, the affirmed license information is determined as a second checking license information in step 153. In case of a negative result of the checking 152, a second checking license information is obtained via the user interface 25 of the electrosurgical generator 10 in step 154.

In step 155, a checking link of the determined or obtained second checking license information and the checking identification information is generated and provided to each of the modules 20, 20' as a valid link and stored at each of the modules 20, 20'.

If the result of the checking 114 whether the checking link is valid is negative, it may also be determined in a step 161, and again analogously to steps 141 and 151, if the checking identification information matches with the identification information, based on which the checking link is generated and also if the checking license information matches with the license information, based on which the checking link is generated. If the result of the determining 161 is negative, i.e. neither serial number nor license keys indicated by the respective information are matching, it is then checked in a step 162, whether an affirmed identification information and an affirmed license information can be obtained based on identification information, license information and/or a link of an identification information and a license information available to or stored at the modules 20, 20'. If the result of the checking 162 is positive, the affirmed identification information is determined as a second checking identification information and the affirmed license information is determined as a second checking license information in a step 163. If the result of the checking 162 is negative, the second checking identification information and the second checking license information are obtained via the user interface 25 of the electrosurgical generator 10 in a step 164. In a step 165, a checking link of the second checking identification information and the second checking license information is generated and provided to each of the modules 20, 20' as a valid link and stored at each of the modules 20, 20'.

Figure 4:
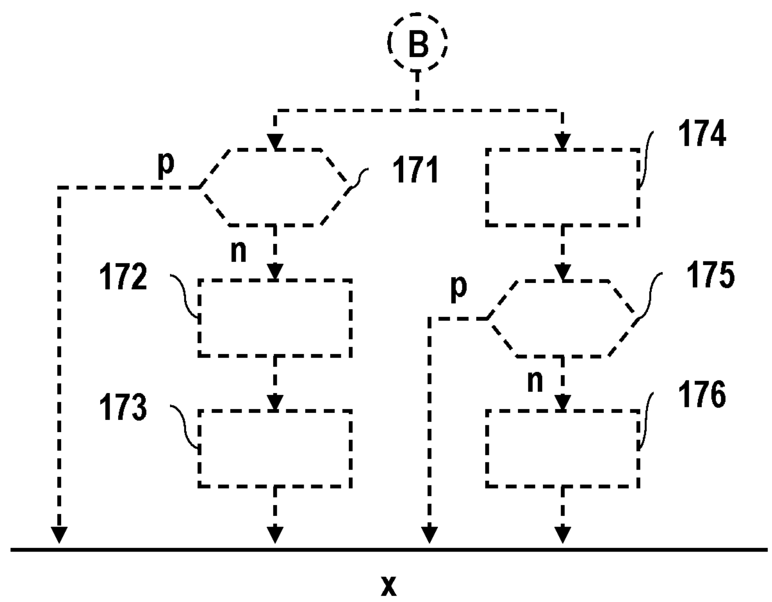

The method 100 of the described embodiment also comprises a method part B, as illustrated by way of the exemplary schematic flow diagram of a section of the method 100 in FIG. 4. The method part B describes additional or alternative method steps considering one of the modules 20, 20' to be designed as a master module having an identification information and a license information available as stored information.

In this scenario, the identification information available at the master module is provided in step 103 to each of the other modules 20, 20'. This identification information is also determined in step 111 as the checking identification information, while the license information available at the master module is determined in step 112 as the checking license information. The checking link is determined in step 113 by generating, at the master module, a master link of the identification information available at the master module and the license information available at the master module and determining the master link as the checking link. Accordingly, this checking link will be checked as valid in step 114 and provided and stored as a valid link at each of the modules in step 115.

In a step 171 it is checked, whether at any of the modules 20, 20', including the master module, an identification information or a link of an identification information and a license information is available. If there are modules 20, 20', at which an identification information is not available, the identification information available at the master module is provided to these modules 20, 20' in a step 172. Additionally, if there are modules 20, 20', at which a link of an identification information and a license information is not available, the checking link generated at the master module is provided to each of the modules 20, 20' in a step 173. In case it is the master module, at which an identification information is not available, for example due to an installation of a new master module out of the factory, the identification information may be obtained via the user interface 25.

Additionally, for example in a scenario, in which a new master module is installed in a generator 10 in the field, in a step 174, any of the links of an identification information and a license information stored at the other modules 20, 20' are received at the master module. It is then checked in a step 175, dependent on the identification information and the license information available at the master module, whether the received links are valid. If the result of any of the checking 175 is negative, a license information is obtained in a step 176 via the user interface 25 of the electrosurgical generator 10 and accordingly made available to the master module.

Figure 5:
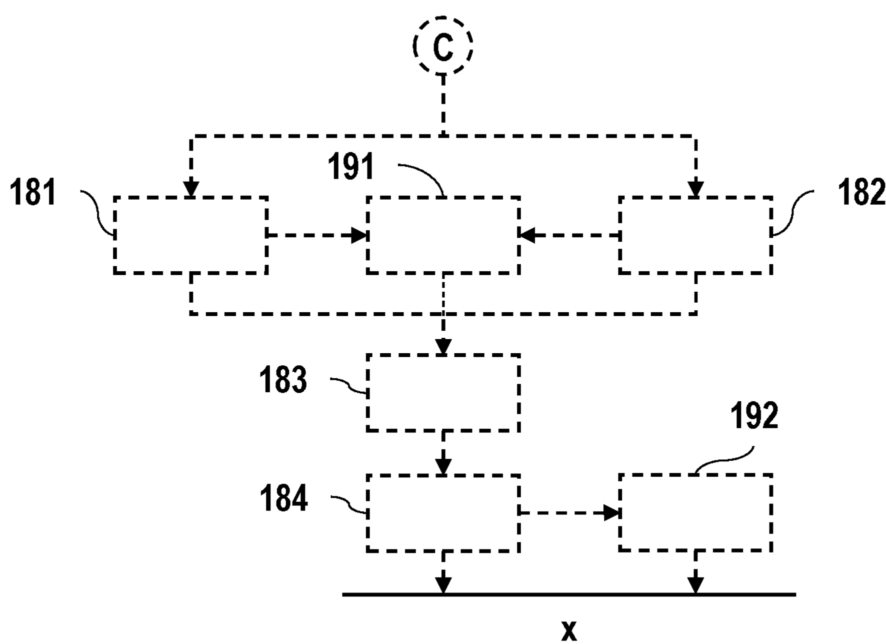

In an embodiment, in which each of the modules 20, 20' is configured to have the identification information and the license information available, e.g., stored in the data storage 24, 24', the method 100 may comprise the method part C, as illustrated in the exemplary schematic flow diagram of a section of the method 100 in FIG. 5.

Identification information and/or license information is obtained either via the user interface 25 of the generator 10 in a step 181 or from at least one of the modules 20, 20' in a step 182. In a step 183 the obtained identification and/or license information is provided to any of the modules 20, 20', at which the respective information is not available. In a step 184 at each of the modules 20, 20' the link of the identification information and the license information available at the respective module 20, 20' is generated and stored in the data storage 24, 24'.

Additionally, the obtaining of steps 181 and 182 comprises a step 191 of providing the identification information available at the master module to each of the modules 20, 20'. It is then also determined in a step 192 at each of the modules 20, 20', dependent on the provided identification information and license information available at the respective module 20, 20', if the link of an identification information and license information stored at the respective module is valid.

Figure 6:
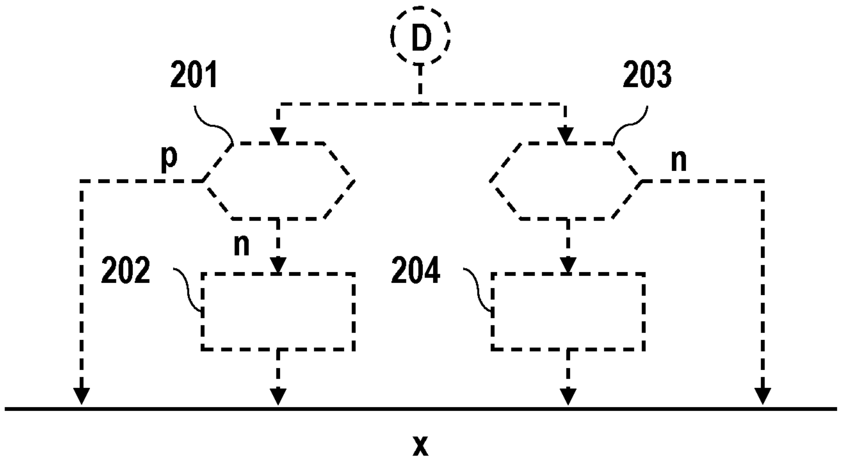

In an embodiment, in which the identification information is available, e.g., stored, at each of the modules 20, 20', the method 100 comprises method part D, as illustrated in the exemplary schematic flow diagram of a section of the method 100 in FIG. 6.

In a step 201 it is checked, whether the identification information available at each of the modules 20, 20 are matching. If the result of the checking 201 is negative, an identification information is obtained via the user interface 25 of the electrosurgical generator 10 in a step 202. Additionally, it is checked in a step 203, whether a license information is available at at least one of the modules 20, 20'. In case of a positive result of the checking 203, a link of the identification information and license information is then generated in a step 204 and provided to each of the modules 20, 20' and stored in data storage 24, 24'.

This enables efficient operation of an electrosurgical generator 10 of modular design, specified by a predetermined license key. In order to provide a functionality of the modules 20, 20' according to the license key, the identification information itself is present at each of the modules 20, 20' in addition to the link of this identification information and a license information. For a verification of the license key, by means of which the link has been generated, the availability of the license information is required only for one module, which may for example, specifically configured for providing a license information.

The embodiments of the invention described in this specification and the optional features and characteristics indicated in each case with respect thereto shall also be understood as disclosed in all combinations with each other. In particular, the description of a feature encompassed by an embodiment—unless explicitly stated to the contrary—shall also not be understood herein as meaning that the feature is indispensable or essential for the embodiment.

The invention claimed is:

1. A method for operating an electrosurgical generator configured to supply power to an electrosurgical instrument, the electrosurgical generator being identifiable by a serial number and comprising at least two modules, wherein the modules are embodied as hardware modules and/or as software modules, wherein each of the modules has a functionality according to an operation mode which is at least partially specified by a license key, wherein in an initializing process of the electrosurgical generator, identification information being indicative of a serial number is available or is made available at at least one of the modules and license information being indicative of a license key is available or is made available at at least one of the modules, each of the modules provides any of the identification information and the license information being available or being made available to it to at least one other of the modules, at least one of the modules generates a link of the identification information and the license information and provides the generated link to each of the other modules, and each of the modules stores the generated link.

2. The method according to claim 1, wherein the making available the identification information or the license information comprises obtaining the respective information via a user interface of the electrosurgical generator.

3. The method according to claim 1, further comprising:

determining a checking identification information from the identification information available at at least one of the modules, determining a checking license information from the license information available at at least one of the modules, and determining a checking link of an identification information and a license information from the links stored at at least one of the modules;

checking, dependent on the checking identification information and the checking license information, whether the checking link is valid; and if the result of the checking is positive, providing the checking link to each of the modules as a valid link; and storing the valid link at each of the modules.

4. The method according to claim 3, wherein determining a checking link of an identification information and a license information from the links stored at at least one of the modules further comprises:

checking, whether a link is stored at more than one of the modules;

if the result of the checking is negative, determining the stored link as the checking link, and if the result of the checking is positive, determining, from the stored links, the checking link based on a majority decision.

5. The method according to claim 3, wherein, if the result of the checking whether the checking link is valid is negative, the method further comprises:

checking, whether matching identification information and matching license information are available at more than one, of the modules; and if the result of the checking is positive, then generating a link of the corresponding identification information and the corresponding license information and providing the generated link to each of the modules as a valid link.

6. The method according to claim 3, wherein, if the result of the checking whether the checking link is valid is negative, the method further comprises:

determining, if the checking identification information matches with the identification information, based on which the checking link is generated and if the checking license information matches with the license information, based on which the checking link is generated;

if the checking identification information is determined to not match with the identification information, based on which the checking link is generated, and the checking license information is determined to match with the license information, based on which the checking link is generated, checking, whether an affirmed identification information can be obtained based on identification information and/or a link of an identification information and a license information available to or stored at the modules, if the result of the checking is positive, determining the affirmed identification information as a second checking identification information, and if the result of the checking is negative, obtaining a second checking identification information via a user interface of the electrosurgical generator;

generating a checking link of the second checking identification information and the checking license information, providing the checking link to each of the modules as a valid link; and storing the valid link at each of the modules.

7. The method according to claim 3, wherein, if the result of the checking whether the checking link is valid is negative, the method further comprises:

determining, if the checking identification information matches with the identification information, based on which the checking link is generated and if the checking license information matches with the license information, based on which the checking link is generated;

if the checking license information is determined to not match with the license information, based on which the checking link is generated, and the checking identification information is determined to match with the identification information, based on which the checking link is generated, checking, whether an affirmed license information can be obtained based on license information and/or a link of an identification information and a license information available to or stored at the modules, if the result of the checking is positive, determining the affirmed license information as a second checking license information, and if the result of the checking is negative, obtaining a second checking license information via a user interface of the electrosurgical generator;

generating a checking link of the second checking license information and the checking identification information, providing the checking link to each of the modules as a valid link; and storing the valid link at each of the modules.

8. The method according to claim 3, wherein, if the result of the checking whether the checking link is valid is negative, the method further comprises:

determining, if the checking identification information matches with the identification information, based on which the checking link is generated and if the checking license information matches with the license information, based on which the checking link is generated;

if the result of the determining is negative, checking, whether an affirmed identification information and an affirmed license information can be obtained based on identification information, license information and/or a link of an identification information and a license information available to or stored at the modules, if the result of the checking is positive, determining the affirmed identification information as a second checking identification information and the affirmed license information as a second checking license information, and if the result of the checking is negative, obtaining the second checking identification information and the second checking license information via a user interface of the electrosurgical generator;

generating a checking link of the second checking identification information and the second checking license information, providing the checking link to each of the modules as a valid link; and storing the valid link at each of the modules.

9. The method according to claim 1, wherein one of the modules of the electrosurgical generator is designed as a master module, having an identification information available by having stored the identification information or by obtaining the identification information via a user interface of the electrosurgical generator, and wherein the identification information available at the master module is provided to each of the other modules and/or wherein the checking identification information is determined from the identification information available at the master module.

10. The method according to claim 9, wherein the license information is available at the master module, or the license information is made available at the master module by obtaining the license information from at least one of the other modules or by obtaining the license information via the user interface of the electrosurgical generator, wherein the identification information available at the master module is determined as a checking identification information, wherein the license information available or made available at the master module is determined as a checking license information, and wherein the checking link of an identification information and a license information from the links stored at at least one of the modules is determined by generating, at the master module, a master link of the identification information available at the master module and the license information available at the master module and determining the master link as the checking link.

11. The method according to claim 10, further comprising:

checking, whether at any of the modules an identification information or a link of an identification information and a license information is available;

providing the identification information available at the master module to each of the modules, at which an identification information is not available, and providing the checking link generated at the master module to each of the modules, at which a link of an identification information and a license information is not available.

12. The method according to claim 11, further comprising:

receiving, at the master module, any of the links of an identification information and a license information stored at the other modules;

checking, dependent on the identification information and the license information available at the master module, whether the received links are valid; and if the result of any of the checking is negative, making available a license information at the master module by obtaining the license information via the user interface of the electrosurgical generator.

13. The method according to claim 11, wherein if an identification information is not available at the master module, obtaining the identification information via the user interface of the electrosurgical generator.

14. The method according to claim 9, wherein each of the modules is configured to have the identification information and the license information available, further comprising:

obtaining identification and/or license information via the user interface of the electrosurgical generator or obtaining identification and/or license information from at least one of the modules and providing the obtained identification and/or license information to any of the modules, at which the respective information is not available;

generating, at each of the modules, a link of the identification information and the license information available at the respective module and storing the generated link.

15. The method according to claim 14, wherein the obtaining identification information comprises providing, to each of the modules, the identification information available at the master module; and wherein the method further comprises:

determining, at each of the modules, dependent on the provided identification information and the license information available at the respective module, if the stored link of an identification information and a license information at the respective module is valid.

16. The method according to claim 1, wherein an identification information is available at each of the modules, and wherein the method further comprises:

checking, whether the identification information available at each of the modules are matching, and, if the result of the checking is negative, obtaining an identification information via a user interface of the electrosurgical generator; and checking, whether a license information is available at at least one of the modules, and if the result of the checking is positive, generating a link of the identification information and the license information, providing the generated link to each of the modules and storing the generated link at each of the modules.

17. An electrosurgical generator, configured to supply power to an electrosurgical instrument and being identifiable by a serial number, comprising a processor, a communication interface, and at least two modules, wherein the modules are embodied as hardware modules and/or as software modules, wherein each of the modules has a functionality according to an operation mode which is at least partially specified by a license key and comprises a data storage for storing at least a link of a license information indicative of the license key and an identification information indicative of the serial number and a communication interface, the electrosurgical generator further comprising a computer-readable medium, the medium having stored therein instructions which, when executed by the processor, cause the method according to claim 1.

* * * * *